（12) United States Patent
Rida et al.

(10) Patent No.: US 10,589,275 B2
(45) Date of Patent: Mar. 17, 2020

(54) SAMPLE COLLECTION AND PROCESSING DEVICE

(71) Applicant: Debiopharm International S.A., Lausanne (CH)

(72) Inventors: Amar Rida, Lausanne (CH); Sélène Ferrari, Lausanne (CH)

(73) Assignee: DEBIOPHARM INTERNATIONAL S.A., Lausanne (CH)

( * ) Notice: Subject to any disclaimer, the term of this patent is extended or adjusted under 35 U.S.C. 154(b) by 0 days.

(21) Appl. No.: 15/315,707

(22) PCT Filed: Jun. 1, 2015

(86) PCT No.: PCT/IB2015/054150
§ 371 (c)(1),
(2) Date: Dec. 1, 2016

(87) PCT Pub. No.: WO2015/186049
PCT Pub. Date: Dec. 10, 2015

(65) Prior Publication Data
US 2017/0095816 A1    Apr. 6, 2017

(30) Foreign Application Priority Data
Jun. 1, 2014 (CH) .................................... 00838/14

(51) Int. Cl.
*B01L 3/00* (2006.01)
*G01N 1/34* (2006.01)

(52) U.S. Cl.
CPC ............ *B01L 3/50825* (2013.01); *G01N 1/34* (2013.01); *B01L 2200/0668* (2013.01);
(Continued)

(58) Field of Classification Search
CPC ......... B01L 3/50825; B01L 2200/0668; B01L 2300/042; B01L 2300/046;
(Continued)

(56) References Cited

U.S. PATENT DOCUMENTS 3,525,254 A    8/1970 Milanes
2009/0148882 A1*  6/2009 Goldstein ............... B01L 3/508
                                                        435/29
(Continued)

FOREIGN PATENT DOCUMENTS

CN    103108959 A    5/2013
JP    10-257881 A    9/1998
(Continued)

OTHER PUBLICATIONS

Weisel, J. (2005). "Fibrinogen and Fibrin." Advances in Protein Chem. 70:247-299 (Year: 2005).*
(Continued)

*Primary Examiner* — Jill A Warden
*Assistant Examiner* — Jacqueline Brazin
(74) *Attorney, Agent, or Firm* — Seed Intellectual Property Law Group LLP (57) ABSTRACT

A device for separating and concentrating target particles or molecules from a fibrinogen containing sample of liquid comprises a container (1) for collecting the sample and a closure (2). The container (1) comprises a first end and a second end and at least one interior wall defining a reservoir portion (5) for receiving the sample. The reservoir portion (5) comprises at least one anchor element (4) to locally catch a polymerized fibrin pellet formed upon the addition of the sample into the container. The separation and concentration process is operated by trapping the target particles or molecules into the so-formed polymerized fibrin pellet that are captured on the anchor element (4).

19 Claims, 6 Drawing Sheets

(52) U.S. Cl.
CPC ..... *B01L 2200/16* (2013.01); *B01L 2300/042* (2013.01); *B01L 2300/046* (2013.01); *B01L 2300/0609* (2013.01); *B01L 2300/0832* (2013.01); *B01L 2300/0851* (2013.01); *B01L 2300/161* (2013.01)

(58) Field of Classification Search
CPC ..... B01L 2300/0832; B01L 2300/0851; B01L 2300/161; G01N 1/34
USPC ........................................... 422/500
See application file for complete search history.

(56) References Cited

U.S. PATENT DOCUMENTS

2009/0158861 A1* 6/2009 Tanner .................. B01L 3/021 73/864.11
2012/0329148 A1* 12/2012 Hur ..................... B01D 63/088 435/309.1
2013/0109009 A1* 5/2013 Kessel ................ B01F 11/0008 435/5

FOREIGN PATENT DOCUMENTS

| WO | 2009/121034 A2 | 10/2009 |
| WO | WO 2009121034 | * 10/2009 |
| WO | 2012/035508 A2 | 3/2012 |
| WO | 2013/006550 A1 | 1/2013 |

OTHER PUBLICATIONS

Seegers, "Purification of Prothrombin and Thrombin: Chemical Properties of Purified Preparations," *J. Biol. Chem.* 136:103-111, 1940. (Downloaded from http://www.jbc.org/ on Nov. 3, 2017.).

* cited by examiner

SAMPLE COLLECTION AND PROCESSING DEVICE

FIELD OF THE INVENTION

The invention relates to a device for liquid sample collection, in particular for the collection of liquid biological samples, and processing with the objective to diagnose or characterise target molecules or particles that may be present in the sample. More specifically, the invention concerns a device suitable for sample preparation allowing effective separation and concentration of target molecules or particles from samples.

DESCRIPTION OF THE RELATED ARTS

In bioassays the ability to extract, concentrate and purify target molecule(s), particle(s) or analyte(s) from diverse samples (i.e. sample preparation) represents a critical step and is challenging as a prerequisite step for effective target detection and analysis. The sample preparation step is the major rate-limiting step in bioassays in terms of detection limit, reproducibility and interferences with other compounds of said particle(s) or analyte(s). Typical existing sample preparation procedures involve lengthy manual or complex robotic pipeting steps including long centrifugation rounds. Not only are such procedures slow, costly and labor consuming but they also can represent a health risk to the laboratory staff demanding expensive disposal of hazardous chemicals. Moreover, the workflow for sample preparation, especially for the new generation of molecular targets has become even more complex and multiple solutions are being offered. Currently, different and individual solutions for sample preparation are being used for each sample type and target. Providing a standard sample preparation workflow solution applicable for multiple samples and targets that are easy-to-implement, compatible with automation and reagent integration and involve minimal hands-on time, still remains an unresolved requirement in the life sciences and diagnostic environment. Further, standardization of sample workflow methodologies is a major requirement mainly in regulated diagnostic environments.

Up to date, there are two methodologies for assay processing: (1) Homogenous assays that operate between analytes at the molecular level in solution. The reaction rates in these assays are fast, since they take place in the liquid phase, and their implementation is relatively straightforward. However, their low specificity and strong susceptibility to medium interferences are major limitations that preclude their use without further sample processing steps. (2) Heterogeneous assays contain a solid surface with molecular recognition group(s) that "selectively" bind and separate target analytes prior to their detection in solution. This provides excellent specificity but at the expense of slow reaction rates between the analytes and the solid surface and also high potential of non-specific binding on the solid surface. Reconciliation of both types of assays during a single process would open the possibility to design more sensitive, precise and rapid diagnostics tools. Indeed, being able to control the molecular interaction as well as the specificity of the recognition at the molecular level and also at the same time performing a controlled separation as for a solid surface will open new perspectives in bio-assays.

International patent application WO2012035508 discloses a method that uses fibrinogen as a vehicle for separating target molecules or particles particle from virtually any kind of samples, instead of state-of-art approaches that use solid surfaces such as magnetic beads or microwells coated with different affinity group as a means to capture and separate targets from samples. In the WO2012035508 methodology, target separation is achieved by converting the fibrinogen vehicle to fibrin which leads to their aggregation in a fibrin network that will retract into a small pellet and separate from the sample. Based on interactions between free molecules in suspension (i.e. homogenous conditions), the reaction between the targets and the fibrinogen vehicle is very fast and efficient. However, the method as disclosed in WO2012035508 still suffers from a limitation related to handling the fibrin pellet during the separation process. In particular it does not address problems associated with the physical handling of the fibrin pellet.

Thus, there is still a need for a new device and method allowing an easy and automated handling of fibrin pellet formed according to the method disclosed in WO2012035508, which will open the possibility of providing a new homogenous sample processing approach that overcomes the complexity of the existing solid surface based methodologies.

BRIEF DESCRIPTION OF THE INVENTION

The instant invention discloses a device for separating and concentrating target particles or molecules from a fibrinogen-containing liquid sample that, when introduced into a container of the device, is capable of forming a polymerized fibrin pellet in which target particles or molecules are trapped, the device comprising: a container for collecting the sample and preferably a closure. The container comprises a first top end and a second bottom end and at least one interior wall defining a reservoir portion for receiving the sample, wherein said reservoir portion comprises at least one anchor element configured to locally hook with a polymerized fibrin pellet formed upon the addition of the said sample to the container and wherein the target particles or molecules are trapped within the polymerized fibrin pellet.

The polymerized fibrin pellet that traps the targets within the device according to the invention is realized according to the method described in patent application WO2012035508, the content thereof is incorporated herein by way of reference. With this respect, the instant invention relates to a device for separating and concentrating target particles or molecules from a fibrinogen-containing liquid sample, the device comprising: a container for collecting the sample and preferably a closure. The container comprises a first top end and a second bottom end and at least one interior wall defining a reservoir portion for receiving said sample, wherein said reservoir comprises at least one anchor element configured to locally hook with a polymerized fibrin pellet formed upon the addition of the said sample to the container. The target particles or molecules are trapped within the polymerized fibrin pellet formed upon the conversion—at least partial—of the fibrinogen contained in the sample into fibrin.

The instant invention also discloses a method for separating and concentrating target particles or molecules from a fibrinogen containing sample where in operation comprises the steps:

(a) adding the said sample to the device container,
(b) converting the fibrinogen within the sample at least partially into fibrin, thereby forming a fibrin network that will trap the target molecules or particles,
(c) retracting the formed fibrin network of step (b) into a small pellet hooked around the device's anchor element, and (d) separating the polymerized fibrin pellet of step (b) from the surrounding sample medium.

The device of the instant invention, upon use, leads to the formation of a small fibrin pellet in which target particles or molecules are trapped and concentrated. The so-formed fibrin pellet is locally captured by the anchor element located within the device's container, which allows its easy separation from the surrounding liquid medium.

Further, the target concentration rate is determined by the size of the so formed fibrin pellet. Therefore, the device composition and design is such that it will result in the formation of a clot with a size that is at most $\frac{1}{3}$ of the initial sample size and preferably the clot size is at most $\frac{1}{10}$ of the initial sample volume. Moreover, in a preferred embodiment of the invention, the clot retracts to further form a small pellet with a size that may reach values that are between $\frac{1}{50}$ and $\frac{1}{1000}$ of the initial sample volume.

Accordingly, the present invention discloses a device that uses fibrinogen as vehicle molecule to separate any target molecule or particle from virtually any kind of sample. The separation mechanisms involve two procedures: (1) a size separation by capturing the targets within the fibrin network upon subjecting of the sample to thrombin or thrombin like enzymes, (2) affinity capture of the target particles or molecules on the fibrinogen in suspension and the separation of the captured target in a fibrin network upon subjecting the sample to thrombin or thrombin-like enzymes. In the latter case, the affinity capture can be due to a native affinity of the target to the fibrinogen molecule. In another embodiment, the affinity capture can be realized by a molecule composed of fibrin/fibrinogen-binding moiety and a target-capturing moiety.

The method according to the invention can further include a step where the so-produced fibrin pellet is lysed to recover the targets. This lysis step is achieved upon resuspending the fibrin pellet concentrate into an appropriate buffered solution. A typical example of a controlled buffer is a hypotonic buffer, buffer-containing detergents in combination with fibrinolytic like plasmin and/or proteolytic agents like Proteinase K, Pronase and metalloproteinase. Such lysis step can be improved by further adding clot lysis enhancers like plasminogen or plasminogen activator. In a preferred embodiment the lysis step can further include the use nucleic acid degradation enzymes.

Size trapping within the fibrin network as well as specific affinity binding reactions may be employed for the determination or isolation of a wide range of target substances in biological samples. Examples of target substances are cells, cell components, cell subpopulations (both eukaryotic and prokaryotic), bacteria, viruses, parasites, antigens, specific antibodies, toxins, proteins, nucleic acid sequences and the like.

A main aspect of the invention concerns a device for separating target molecules or particles from a fibrinogen containing sample, according to independent claim 1.

Another main aspect of the invention concerns a method for separating target molecules or particles from a sample according to claim 15.

Different embodiments are set out in the dependent claims. The subject matter of the claims and all claimed combinations is incorporated by reference in this description and remains part of the disclosure even if claims are abandoned.

BRIEF DESCRIPTION OF THE DRAWINGS

The objects and features of the present invention are set forth with particularity in the appended claims. The present invention, both as to its organization and manner of operation, together with further objects and advantages, may best be understood by reference to the following description, taken in connection with the accompanying drawings, wherein

Figure 1:
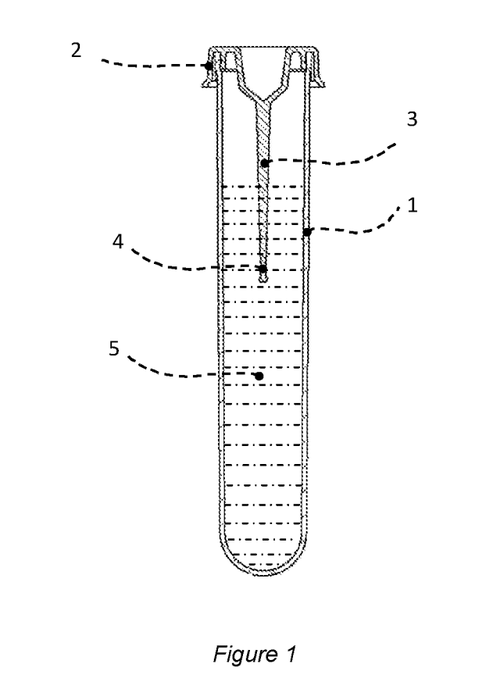
FIG. 1 is a schematic representation of a preferred embodiment of the device according to the invention.

FIG. 1 is a schematic representation of a preferred embodiment of the device for separating and concentrating target particles or molecules out a sample of liquid comprising a container (1) for collecting the sample and a closing cap (2) positioned on the open first top side of the container. The container further comprises a second closed bottom end and at least one interior wall defining a reservoir portion (5) for receiving the sample. The closing cap (2) comprises an elongated downwardly-protruding pin element (3) immersed in the sample in the device's reservoir (5) and comprising at its lower end an anchor element (4).

Figure 2:
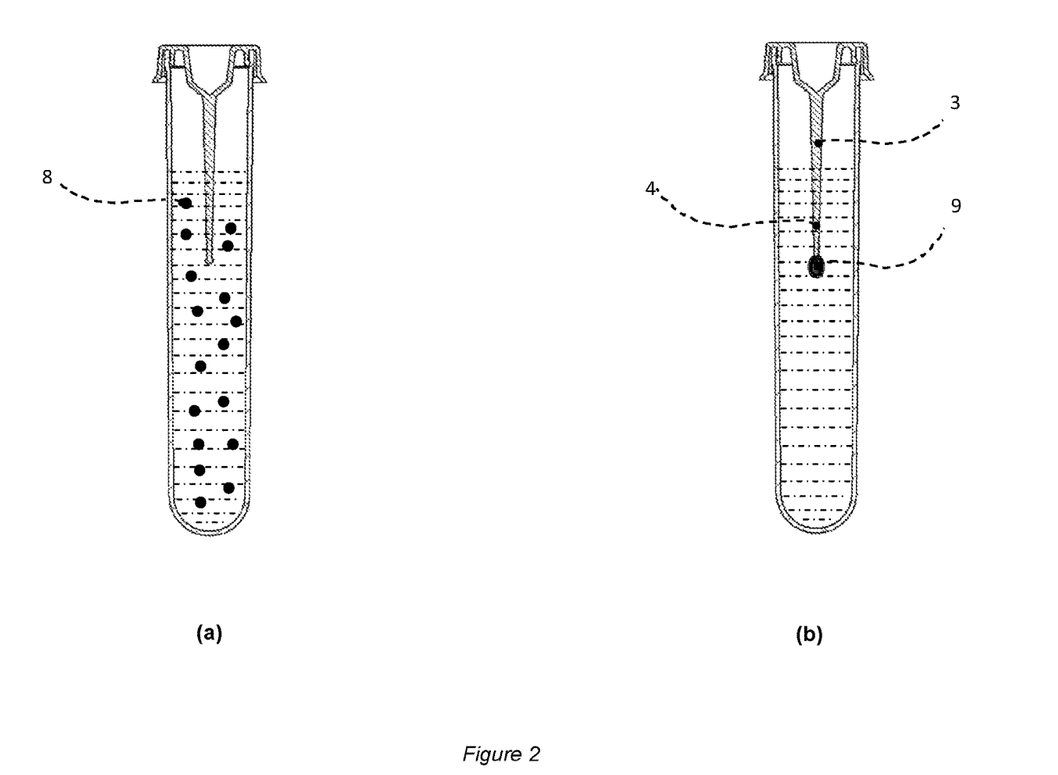
FIG. 2(a) and FIG. 2(b) are schematic representations of operation of the device.

FIG. 2 is a schematic representation of the device operation for the separation and concentration of target particles or molecules from a sample. As shown in FIG. 2 (a) the device according to the invention is designed to receive a liquid sample that may include target particles or molecules (8) to be separated or concentrated. The sample may include fibrinogen as a native component (e.g. blood). In the case of a fibrinogen-free sample to be processed, the container (1) should include fibrinogen as an additive to be mixed with the fibrinogen-free sample. FIG. 2 (b) shows that as the sample is added to the device, the fibrinogen within the liquid (either native from the sample or not) will be converted at least partially to fibrin upon subjecting the sample to thrombin or thrombin-like enzymes, thereby forming a fibrin network that will trap the target molecules or particles. The so-formed fibrin network will retract to form a polymerized fibrin pellet (9) hooked or adhered around the anchor element (4).

Figure 3:
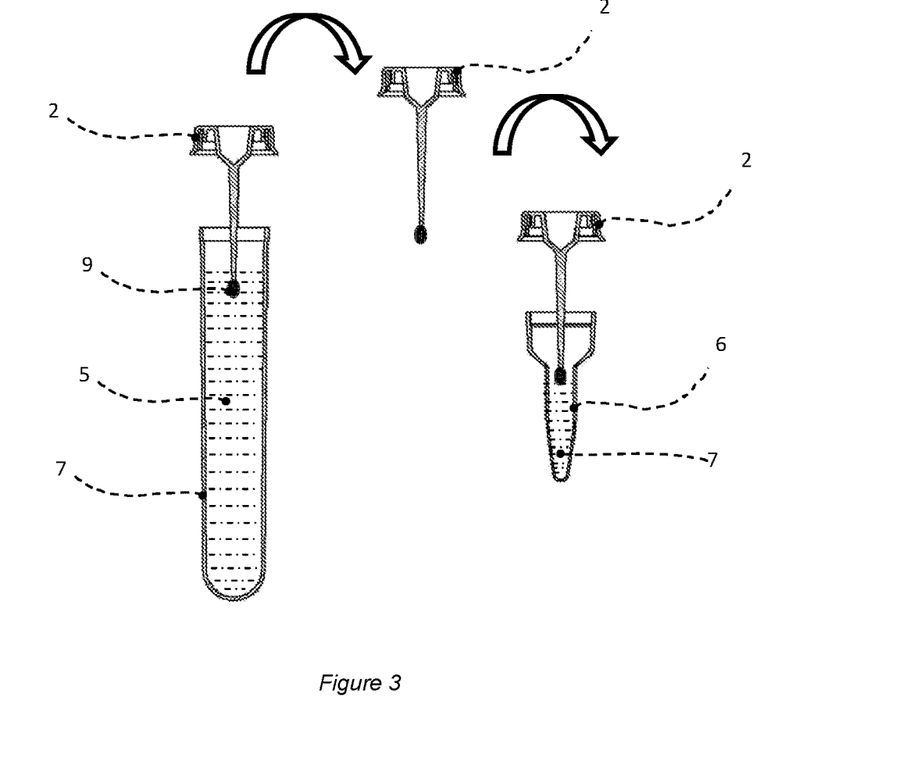
FIG. 3 illustrates separation and concentration of target particles or molecules.

FIG. 3 is a schematic representation of the device operation for the separation and concentration of target particles or molecules from a sample. Upon retraction of the fibrin network into a polymerized fibrin pellet (9) hooked around the anchor element (4), the closure cap (2), with the anchor element (4) and the hooked polymerized fibrin pellet (9), will be removed from the container (1), thereby separating the polymerized fibrin pellet (9), with the trapped targets, from the sample medium. In a subsequent step, the closure cap (2) can be immersed in a secondary container (6) containing resuspending liquid medium (7) that will lyse the fibrin pellet, thereby allowing recovery of the target molecules or particles (8). Secondary container (6) is preferably smaller than the device according to the present invention.

Figure 4:
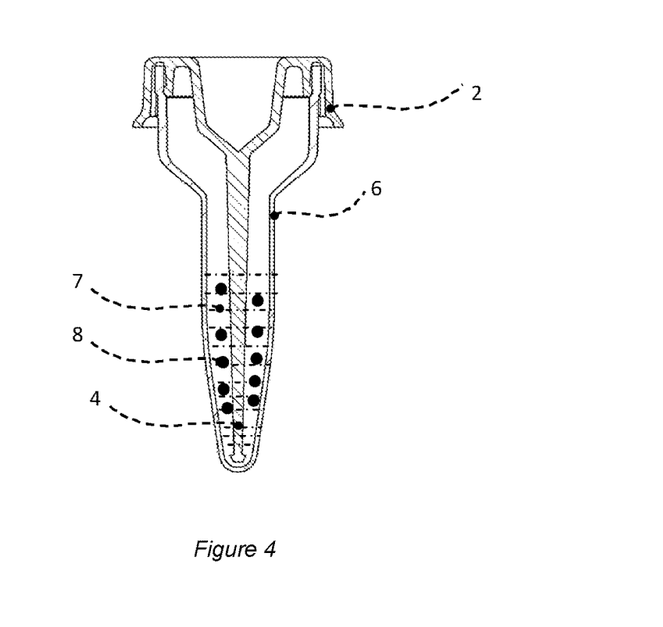
FIG. 4 illustrates a secondary container for target recovery and suspension.

FIG. 4 is a schematic representation of a preferred embodiment of the target recovery and resuspension device comprising a smaller secondary container (6) for containing the resuspending liquid. The container (6) comprises an open first top end that is adapted to receive a cap, such as the closure cap (2), comprising anchor element (4) of the device according to the invention. The container (6) further comprises a second closed bottom end and at least one interior wall defining a reservoir portion (7) for containing the resuspension liquid that allows to lyse the fibrin pellet and thereby recover the targets (8). Target recovery is achieved by immersing anchor element (4) of closure cap (2) into the recovery container (6).

Figure 5:
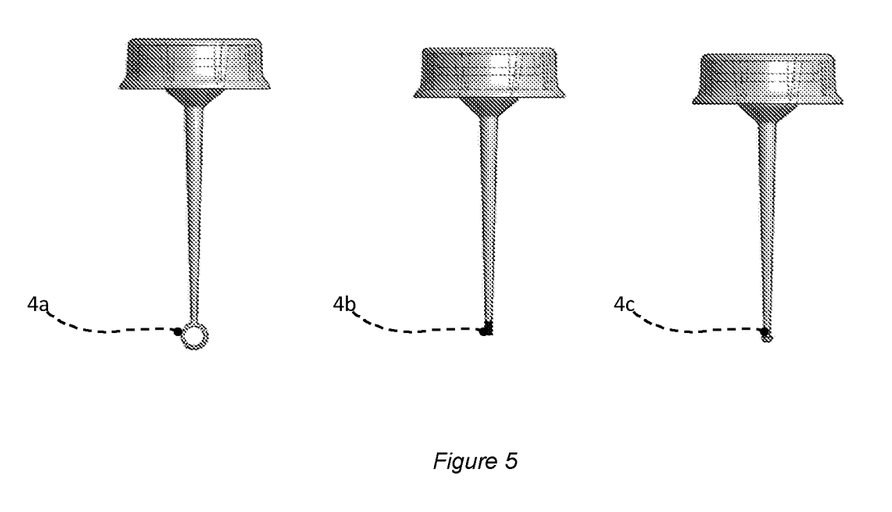
FIG. 5 shows three different types of anchor element.

FIG. 5 shows different embodiments of the anchor element (4): namely (4a) ring shape, (4b) chemical or biological coating and (4c) irregular hook shape.

Figure 6:
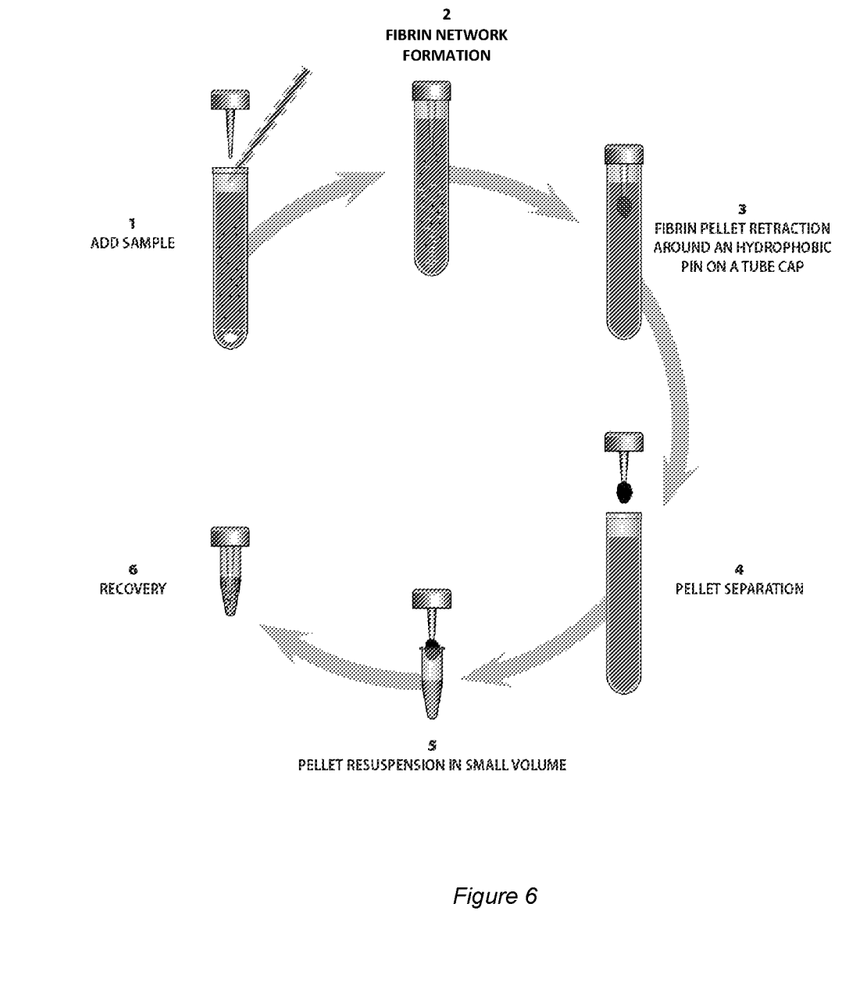
FIG. 6 is a diagram of overall operation, and FIGS. 7 (a), (b) and (c) show a further embodiment of the device in three different states.

FIG. 6 is a schematic representation of overall operation of the method for separating and concentrating target particles or molecules from a fibrinogen-containing sample using the device according to the invention. In step 1, sample is added to the device's container. In step 2 there is a fibrin network formation reaction. In step 3, the fibrin pellet retracts around a hydrophobic pin (anchor element) fitted on the tube cap. Step 4 is a pellet separation phase. In step 5 the pellet is immersed in a small volume of resuspension solution. Finally, in step 8, the target particles or molecules are recovered.

Figure 7:
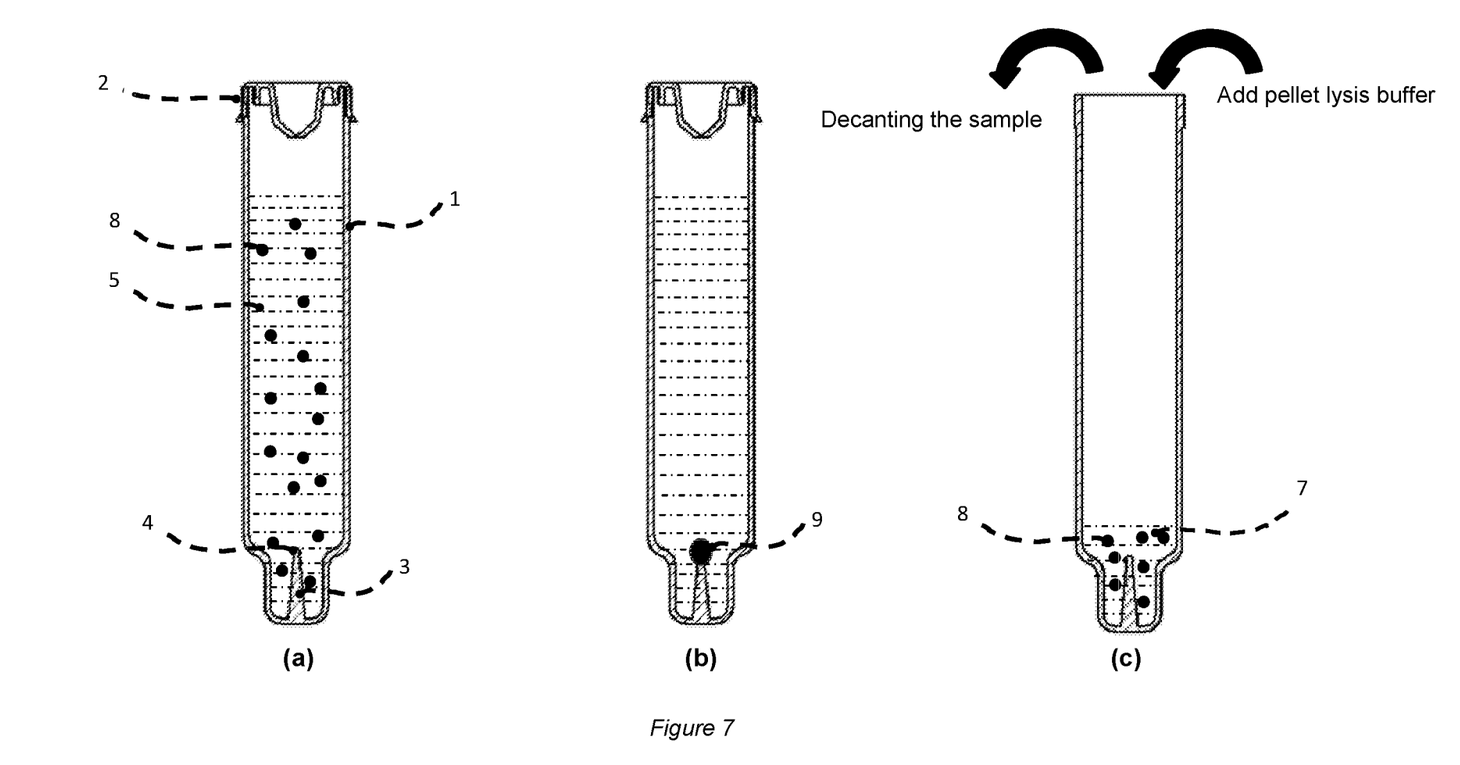

FIG. 7 is a schematic representation of a preferred embodiment of the device for separating and concentrating target particles or molecules from a liquid sample comprising, differentiated with respect to the device of FIG. 1, an upwardly-extending elongated pin element (3) immersed in the reservoir portion (5) and positioned in the closed bottom end of the container (1). The elongated pin element (3) further comprises at its upper end an anchor element (4). In operation, a retracted fibrin network forming a polymerized fibrin pellet (9) will be hooked or adhere around the anchor element (4). The so-formed fibrin pellet can be thereafter separated by decanting the surrounding liquid medium. Target recovery is achieved by adding, to the same container (1), a fibrin pellet lysis buffer (7) that will lyse the fibrin pellet allowing thereby the recovery of the target molecules or particles (8).

DETAILED DESCRIPTION OF THE INVENTION

As illustrated in FIG. 1, a device according to the invention for separating and concentrating target particles or molecules from a fibrinogen containing sample of liquid comprises: a container (1) for collecting the sample and a closure (2). The container (1) comprises a first top end and a second bottom end and at least one interior wall defining a reservoir portion (5) for receiving the sample, wherein the reservoir portion comprises at least one anchor element (4) to locally hook the polymerized fibrin pellet (9) formed upon addition of the sample to the container and wherein target particles or molecules are trapped within the polymerized fibrin pellet.

The invention also covers a method for collecting and processing biological samples comprising: providing a container comprising thrombin and potentially fibrinogen in appropriate concentration to lead to effective separation of target molecules or particles from a surrounding complex liquid medium. This method further allows to recover the target(s) that are highly concentrated within the polymerized material and that preferably have a volume that is at most $\frac{1}{10}$ of the initial sample volume. Furthermore, an advantage of the disclosed method is the capability to reach a concentration rate of $\frac{1}{100}$ to $\frac{1}{1000}$ of the initial sample volume. The so-concentrated target(s) can be thereafter processed very easily through further purification step(s) and/or directly analyzed using state-of-art methodologies.

One major advantage of the disclosed device is to allow an automatic and easy separation of the target particles or molecules by integrating into the device an anchor element (4) that will locally hook, adhere or nucleate the polymerized fibrin pellet. In practice, the anchor element (4) somehow constitutes a "nucleation" point around which the fibrin pellet will be formed and retracted into a small pellet as shown in FIG. 2. In a preferred embodiment, the anchor element (4) is integrated with the closure cap (2) that comprises an elongated pin element (3) to be immersed in the liquid sample contained in the reservoir portion (5) upon closing the cap. In this configuration, the anchor element (4) is located at or towards the end side of the pin element (3).

Integration of the anchor element (4) in the cap has an advantage of allowing an easy separation of the polymerized fibrin pellet (9) hooked around the anchor element (4). As shown in FIG. 3, the closure cap (2) containing anchor element (4) with the hooked polymerized fibrin pellet (9) can be removed from the container (1), thereby achieving the separation of concentrated polymerized fibrin pellet (9), with the targets trapped in it, from the initial sample medium. The closure cap (2) can thereafter be plugged in a smaller container (6) containing resuspending liquid medium (7) for the target recovery, as shown in FIG. 4.

Although the instant invention has been illustrated by a preferred embodiment where the anchor element (4) is integrated in the closure cap, in practice the anchor element can also be part of the device container (1) as for instance integrated into the walls or the bottom sides of the reservoir portion (as shown in FIG. 7). In this case, the separation process will be achieved by decanting the sample from the device container (1) while keeping the fibrin pellet attached (or hooked) to the anchor element (4). The target recovery is achieved by adding, to the same container (1), a fibrin pellet lysis buffer (7) (as shown in FIG. 7 c), that will lyse the fibrin pellet allowing thereby the recovery of the target molecules or particles (8).

The anchor element according to the invention can be any local part with irregular or regular shape like the ones shown in FIG. 5. In preferred embodiments, the anchor element can be a local surface coating that allows local attachment of the fibrin pellet. Non-limiting examples of such coating include chemical coating (e.g hydrophobic coating) and biological coating (e.g. fibrinogen/fibrin binding molecules such as thrombin, clotting factor XIII, bacterial fibrinogen binding proteins and tissue plasminogen activator (t-PA)).

The device as disclosed herein can encompass any sample collection device including tubes such as test tubes and centrifuge tubes; closed system sample collection devices, such as collection bags; syringes, especially pre-filled syringes; catheters; microwells and other multi-well plates; arrays; tubing; laboratory vessels such as flasks, and assemblies; pipettes and pipette tips, etc. In general, the instant invention concerns any container suitable for holding a biological sample, as well as containers and elements involved in transferring samples provided they meet the criteria outlined herein.

Based on the foregoing disclosure, the present invention further includes a method for separating target molecules or particles from a sample using a sample collection device that can be very easily used manually or integrated with state-of-the-art automated systems which makes this sample preparation method easily integrated in routine laboratory work flows as shown in FIG. 6.

The volume of the sample container is between 0.1 to 100 ml and preferably between 0.1 to 10 ml. The concentration of fibrinogen in the sample is preferably at least 0.1 µg/ml.

In a preferred embodiment the concentration of fibrinogen in the sample is between 0.1 to 100 mg/ml and most preferably between 10 mg/ml to 10 μg/ml.

The device may further include as an additive a thrombin or thrombin enzyme. The thrombin concentration is 0.01 to 10 I.U./ml and preferably within the range of 0.1 to 2 I.U./ml of sample. In practice, the quantity of the thrombin or thrombin like enzyme must be adjusted in correspondence to the fibrinogen concentration within the device to obtain the desired fibrin network structure and pellet size. The thrombin amount is preferably less than 20 I.U. thrombin per mg of fibrinogen, preferably in a range between 0.01 to 10 I.U. thrombin per mg of fibrinogen, more preferably between 0.1 to 1 I.U. thrombin per mg of fibrinogen.

In case of blood samples such as whole blood, the sample collection device according to the invention can further include coagulation agents that promote the generation of endogenous thrombin within the sample. Such promoting agents can be for instance selected from groups comprising powdered or fibrous silicate compounds such as kaolin, Celite, diatomaceous silica and glass fibers, fine powders of calcium compounds such as calcium carbonate and calcium sulfate, thrombin-like substances derived from snake venoms, and polyphenols that can activate blood pelleting factors to promote coagulation. Further, these coagulation promoting agents can be, for example, added individually or in combination into the sample or coated inside the wall of sample container. The amount of such promoting agents must be adjusted in a way to control the coagulation process and obtain a small fibrin pellet size.

In a preferred embodiment to control the fibrin network structure in order to trap target molecules or particles from a sample, the sample collection device according to the invention can further include additives that allow to adjust the concentration of calcium. In practice, this can be achieved by adding a calcium ion source to the device. The calcium ion source is preferably Calcium Chloride ($CaCl_2$), preferably in a concentration range between 1 to 10 mg per ml of sample volume, even more preferably between 4 to 7 mg per ml of sample volume, most preferably between 5 to 6 mg per ml of sample volume. In blood samples, for instance, calcium is naturally present and the adjustment of the calcium concentration can be achieved by further adding to the device calcium chelating agents such as GDTA, EDTA or citrate.

Further, the device according to the invention may include additives comprising molecules having: (I) fibrin/fibrinogen-binding moiety and (II) a substance-capturing moiety directed against the target molecules or particles. Accordingly, the substance-capturing moiety directed against the target molecules or particles can be selected from the group comprising antibodies, nucleic acids and aptamers designed to specifically recognize the said target molecules or particles. Further, the substance-capturing moiety can be coupled or combined with a fibrin/fibrinogen-binding moiety selected from the group comprising thrombin, fibronectin, bacterial fibrinogen binding proteins, tissue-type plasminogen activator, integrines and moieties derived from any member of this group. In a preferred embodiment, the fibrin/fibrinogen-binding moiety and the substance-capturing moiety are combined in a fusion molecule.

Further, the device according to the invention can include additives comprising a fibrinogen recombinant protein. Such recombinant fibrinogen protein can be specifically designed to enhance or inhibit affinity interactions of the recombinant fibrinogen protein with specific target molecules or particles contained in the sample under use within the device. In a preferred embodiment, the recombinant protein in use within the device is a fibrinogen fusion protein with a capturing moiety domain directed against the said target molecules or particles. In another embodiment, the fibrinogen fusion protein further includes a degradation site. This will be particular useful for recovering the bound target molecules or particles from the fibrin network during a lysis step. In a preferred embodiment, the degradation site is an enzymatic or hydrolytic degradation site. In a most preferred embodiment, the degradation site is an enzymatic degradation site, which is cleaved by an enzyme selected from the group consisting of plasmin and matrix metalloproteinase.

In practice all of the previously described additives can be added to the sample after the sample collection or already integrated within the device. In the last case, the additives can be integrated solubilized in an aqueous buffer solution. In a preferred embodiment, the said additives can be included within the device in a lyophilized form that can be solubilized just prior to the device use or upon the introduction of the sample into the device.

The sample collection device according to the invention can be used to separate and concentrate target molecules or particles such as target cells, cell components, cell subpopulations (both eukaryotic and prokaryotic), bacteria, viruses, parasites, antigens, specific antibodies, toxins, proteins, nucleic acid sequences and the like.

The sample collection device according to the invention can be used to separate and concentrate target molecules or particles from diverse samples. In general this includes whole blood, blood derivatives, blood components as well as fibrinogen-free samples (including but not limited to urine, sputum and swab). In this respect, the sample herein can refer to any sample type that needs to be tested, including food, clinical, environmental, and experimental samples.

In practice, the device may also include an identification code. Such an identification code can be determined by, without limitation, a code bar or a color added to the device, or by the size and/or shape of the device itself. Such identification code can be used as a reference or indicator of the device's intended use and application. Devices according to several embodiments of the invention can be, in fact, differentiated according to their composition, sample type for which the device will be used and/or the target(s) that need to be separated.

Those skilled in the art will appreciate that various adaptations and modifications of the just-described preferred embodiments can be configured without departing from the scope of the invention. Therefore, it is to be understood that, within the scope of the appended claims, the invention may be practiced otherwise than as specifically described herein.

The invention claimed is:

1. A device for separating and concentrating target particles or molecules from a fibrinogen-containing liquid sample that is capable, when introduced into a container of the device, of forming a polymerized fibrin pellet in which the target particles or molecules are trapped, the device comprising: i) a container for collecting the sample, the container comprising a top end, a bottom end, and at least one interior wall defining a reservoir portion for receiving the sample, wherein the top end is an open end; and ii) a removable closure cap for closing the top end, the closure cap comprising an elongated pin element which extends into the reservoir portion upon closing the closure cap, the pin element comprising at least one anchor element located at or toward an end of the pin element, the anchor element being configured to locally hook the polymerized fibrin pellet comprising the target particles or molecules therein and comprising a local hydrophobic surface coating around which the polymerized fibrin pellet is attached during operation.

2. A device according to claim 1, wherein the volume of the container is between 0.1 to 20 mL.

3. A device according to claim 1, wherein the concentration of fibrinogen within the sample is between 0.1 to 100 mg/mL.

4. A device according to claim 1, wherein the polymerized fibrin pellet is formed within the container upon exposure of the fibrinogen-containing liquid sample to thrombin or a thrombin-like enzyme.

5. A device according to claim 4, wherein the device is configured to receive the thrombin or thrombin-like enzyme after sample collection.

6. A device according to claim 1, wherein the fibrinogen within the fibrinogen-containing sample is native to the sample.

7. A device according to claim 1, wherein the fibrinogen-containing sample is formed from a fibrinogen-free sample in the container.

8. A device according to claim 1, wherein the anchor element forms a shaped hook around which the polymerized fibrin pellet is locally attached during operation.

9. A method for separating and concentrating target particles or molecules from a fibrinogen-containing sample, comprising using a device for separating and concentrating the target particles or molecules from the fibrinogen-containing liquid sample that is capable, when introduced into a container of the device, of forming a polymerized fibrin pellet in which the target particles or molecules are trapped, the device comprising:
   i) a container for collecting the sample, the container comprising a top end, a bottom end and at least one interior wall defining a reservoir portion for receiving the sample, wherein the top end is an open end; and
   ii) a removable closure cap for closing the top end, the closure cap comprising an elongated pin element which extends into the reservoir portion upon closing the closure cap, the pin element comprising at least one anchor element located at or toward the end of the pin element, the anchor element being configured to locally hook the polymerized fibrin pellet comprising the target particles or molecules therein and comprising a local hydrophobic surface coating around which the polymerized fibrin pellet is attached during operation, the method comprising the steps of:
   (a) adding the sample to the device container, (b) converting fibrinogen within the sample at least partially into fibrin, thereby forming a fibrin network that will trap the target molecules or particles, (c) retracting the formed fibrin network of step (b) into a small pellet hooked around the device's anchor element, and (d) separating the polymerized fibrin pellet of step (b) from the surrounding sample medium.

10. A method according to claim 9, wherein the method further comprises the step (e) of resuspending the polymerized fibrin pellet in a liquid medium that allows lysis of the fibrin pellet, thereby recovering the target molecules or particles.

11. A method according to claim 10, wherein a recovery step (e) is achieved by immersing the closure cap in a resuspension container, containing a resuspending liquid medium.

12. A method according to claim 10, wherein a recovery step (e) is achieved by adding a resuspending liquid medium to the container.

13. A method according to claim 9, wherein the size of the polymerized fibrin pellet is at most $\frac{1}{10}$ of the initial volume of the fibrinogen-containing sample.

14. A method according to claim 10, wherein the volume of the liquid medium of step (e) is at most $\frac{1}{10}$ of the initial volume of the fibrinogen-containing sample.

15. A device according to claim 1, wherein the target molecules or particles comprise bacteria, virus, yeast, cells, proteins, peptides or nucleic acids.

16. A device according to claim 1, wherein the container comprises fibrinogen in a lyophilized form.

17. A method according to claim 9, wherein a recovery step (e) is achieved by immersing the closure cap in a resuspension container, containing a resuspending liquid medium.

18. A device according to claim 4, wherein the container comprises the thrombin or thrombin-like enzyme.

19. A device according to claim 18, wherein the thrombin or thrombin-like enzyme is in lyophilized form.

* * * * *

UNITED STATES PATENT AND TRADEMARK OFFICE
CERTIFICATE OF CORRECTION

PATENT NO. : 10,589,275 B2
APPLICATION NO. : 15/315707
DATED : March 17, 2020
INVENTOR(S) : Rida et al.

Page 1 of 1

It is certified that error appears in the above-identified patent and that said Letters Patent is hereby corrected as shown below:

In the Claims

Claim 1, Column 8, Line 67:
"comprising the target particles or molecules therein and"
Should read:
--comprising the target particles or molecules therein, and--

Claim 9, Column 9, Line 41:
"anchor element located at or toward the end of the pin"
Should read:
--anchor element located at or toward an end of the pin--

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*